(12) United States Patent
Bapat et al.

(10) Patent No.: US 8,609,601 B2
(45) Date of Patent: Dec. 17, 2013

(54) PERSONAL CLEANSING COMPOSITION

(75) Inventors: Mohini Anand Bapat, Mumbai (IN); Suman Kumar Bhattacharya, Bangalore (IN); Tapomay Bhattacharyya, Bangalore (IN); Sudipta Ghosh Dastidar, Bangalore (IN); Vijay Mukund Naik, Mumbai (IN); Janhavi Sanjay Raut, Bangalore (IN)

(73) Assignee: Conopco Inc., Englewood Cliffs, NJ (US)

( * ) Notice: Subject to any disclaimer, the term of this patent is extended or adjusted under 35 U.S.C. 154(b) by 0 days.

(21) Appl. No.: 13/129,132

(22) PCT Filed: Nov. 16, 2009

(86) PCT No.: PCT/EP2009/065225
§ 371 (c)(1),
(2), (4) Date: Aug. 12, 2011

(87) PCT Pub. No.: WO2010/057850
PCT Pub. Date: May 27, 2010

(65) Prior Publication Data
US 2012/0094883 A1 Apr. 19, 2012

(30) Foreign Application Priority Data
Nov. 20, 2008 (IN) .......................... 2443/MUM/2008

(51) Int. Cl.
*A61K 8/92* (2006.01)

(52) U.S. Cl.
USPC ........................................ 510/158; 510/159

(58) Field of Classification Search
USPC ................................. 510/158, 159
See application file for complete search history.

(56) References Cited

U.S. PATENT DOCUMENTS

| | | | |
|---|---|---|---|
| 2,697,699 A | 12/1954 | Cohn | |
| 2,982,665 A | 5/1961 | Wilcox | |
| 3,211,565 A | 10/1965 | Bundy | |
| 3,450,666 A | 6/1969 | Nease | |
| 4,637,933 A * | 1/1987 | Zabotto nee Arribau et al. ............................. | 424/617 |
| 4,666,624 A | 5/1987 | Irlam et al. | |
| 4,715,986 A | 12/1987 | Gruning et al. | |
| 4,857,308 A | 8/1989 | Fukasawa et al. | |
| 4,916,095 A | 4/1990 | Fogler et al. | |
| 5,137,568 A | 8/1992 | Durham et al. | |
| 5,317,568 A | 5/1994 | Bixby et al. | |
| 5,449,402 A | 9/1995 | Whalen-Shaw | |
| 5,527,430 A | 6/1996 | Gill | |
| 5,603,411 A | 2/1997 | Williams et al. | |
| 5,871,764 A * | 2/1999 | Diaz et al. ...................... | 424/405 |
| 6,165,485 A | 12/2000 | Alther | |
| 6,288,076 B1 | 9/2001 | Kostyniak et al. | |
| 6,498,134 B1 * | 12/2002 | Scheibel et al. ............... | 510/357 |
| 6,541,440 B2 | 4/2003 | Heininger | |
| 6,649,147 B1 | 11/2003 | Y et al. | |
| 6,774,099 B1 * | 8/2004 | Scheibel et al. ............... | 510/357 |
| 6,794,437 B2 | 9/2004 | Ross | |
| 6,828,288 B2 | 12/2004 | Takeshima | |
| 7,772,181 B2 * | 8/2010 | Amin et al. .................... | 514/18.7 |
| 7,977,302 B2 * | 7/2011 | Chakrabarty et al. ......... | 510/447 |
| 2002/0039986 A1 | 4/2002 | Heininger | |
| 2006/0111259 A1 * | 5/2006 | Chakrabarty et al. ......... | 510/141 |
| 2007/0107635 A1 | 5/2007 | Soane | |
| 2008/0220050 A1 | 9/2008 | Chen et al. | |
| 2009/0246529 A1 | 10/2009 | Bhattacharya et al. | |

FOREIGN PATENT DOCUMENTS

| | | |
|---|---|---|
| CH | 397127 | 8/1965 |
| CH | 397127 A | 8/1965 |
| DE | DD220328 A1 | 3/1985 |
| DE | DD220328 A1 | 3/1985 |
| DE | 19538029 A1 | 4/1997 |
| EP | 0318642 | 9/1987 |
| EP | 0265101 A2 | 4/1988 |
| EP | 0319168 A1 | 6/1989 |
| EP | 0927748 A1 | 7/1999 |
| EP | 2105469 A1 | 9/2009 |
| FR | 93672 | 5/1969 |
| GB | 867752 | 5/1961 |
| GB | 1425177 | 2/1976 |

(Continued)

OTHER PUBLICATIONS

Itagaki et al., Organic modification of the interlayer surface of kaolinite with propanediols by transesterification, J. Mater. Chem., Jan. 10, 2003, 13, 1064-1068, Royal Society of Chemistry 2003.

(Continued)

*Primary Examiner* — Mark Eashoo
*Assistant Examiner* — M. Reza Asdjodi
(74) *Attorney, Agent, or Firm* — Karen E. Klumas

(57) ABSTRACT

This invention relates to a liquid or soft-solid personal cleansing composition that utilises the detergency properties of new materials which are more efficient, more inexpensive and are an environmentally friendly alternative to conventional soaps or synthetic surfactants. It more particularly relates to a cleansing composition in liquid, gel or cream formats. The present invention provides for a personal cleansing composition comprising (i) 1 to 50% of treated clay particles; and (ii) a cosmetically acceptable base; wherein said treated clay particles are asymmetric 1:1 or 2:1:1 clay particles having alternating tetrahedral and octahedral sheets terminating with a tetrahedral sheet at one external surface plane and an octahedral sheet at another external surface plane, with a fatty acid of carbon chain length 10 to 22 attached to coordinating cation on one of said exterior surface planes.

14 Claims, No Drawings

(56) References Cited

FOREIGN PATENT DOCUMENTS

| GB | 2011786 A | 7/1979 |
|---|---|---|
| GB | 710129 A | 11/2012 |
| JP | 62277316 | 12/1987 |
| JP | 2001122749 A | 5/2001 |
| JP | 2004359483 A | 12/2004 |
| WO | WO9905249 | 2/1999 |
| WO | WO2005011622 A1 | 2/2005 |
| WO | WO2005059079 A1 | 6/2005 |
| WO | WO2006053708 A1 | 5/2006 |
| WO | WO2008152417 A2 | 12/2008 |
| WO | WO2009118421 | 10/2009 |
| WO | WO2011020679 A1 | 2/2011 |
| WO | WO2011036029 A1 | 3/2011 |

OTHER PUBLICATIONS

Gardolinski et al., Grafted organic derivatives of kaolinite: I. Synthesis, chemical and reheological characterization, Clay Minerals, Dec. 1, 2005, 40-4, 537-546, Mineralogical Society of Great Britain & Ireland.

Domka, Modification estimate of kaolin, chalk, and precipitated calcium carbonate as plastomer and elastomer fillers, Colloid & Polymer Science, 1994, 272, 1190-1202, A. Mickiewicz University, Poznan.

Viseras et al., Uses of clay minerals in semisolid health care and therapeutic products, Applied Clay Science, 2007, 36, 37-50, Elsevier.

Perro et al., Design and synthesis of Janus micro- and nanoparticles, Journal Materials Chemistry, 2005, 15, 3745-3760.

International Search Report PCT/EP2009/065225 dated May 10, 2011.

EP Search Report EP 09 15 1999 dated Jul. 7, 2009.

PCT International Search Report in PCT application PCT/EP2010/060784 dated Oct. 27, 2010 with Written Opinion (G2004USw).

European Search Report in EP application EP 09 17 3998 dated Mar. 20, 3020 (G2004USw).

PCT International Search Report in PCT application PCT/EP2010/062616 dated Mar. 1, 2011 with Written Opinion (G2014).

European Search Report in EP application EP 09 17 5484 dated Apr. 21, 2010 (G2014).

PCT International Search Report in PCT application PCT1EP2010/062618 dated Nov. 17, 2010 with Written Opinion (G2015USw).

European Search Report in EP application EP 09 17 5488 dated Mar. 16, 2010 (G2015USw).

PCT International Search Report in PCT application PCT/EP2009/053707 dated Jul. 2, 2009 with Written Opinion (T2002USw).

European Search Report in EP application EP 08 16 4175 dated Feb. 23, 2009 (T2002USw).

European Search Report in EP application EP 09 15 5227 dated Jun. 25, 2009 (T2002USw).

PCT/EP20091066500 Written Opinion dated Dec. 7, 2009 (T2005).

European Search Report in EP application EP 12 19 9421 dated Jul. 3, 2013 (J2177).

Dastidar et al., U.S. Appl. No. 13/389,928, filed Jul. 26, 2010.

Bhattacharya et al., U.S. Appl. No. 13/496,898, filed Mar. 19, 2012.

Bhattacharya et al., U.S. Appl. No. 12/411,442, filed Mar. 26, 2009.

Bhattacharya et al., U.S. Appl. No. 12/933,883, filed Sep. 22, 2010.

\* cited by examiner

PERSONAL CLEANSING COMPOSITION

This invention relates to a liquid or soft-solid personal cleansing composition that utilises the detergency properties of new materials which are more efficient, more inexpensive and are an environmentally friendly alternative to conventional soaps or synthetic surfactants which have been used heretofore in such cleansing compositions. The present invention more particularly relates to a cleansing composition in liquid, gel or cream formats.

Cleansing compositions in soft-solid or liquid formats have aesthetic appeal with consumers. These are often used for specialised applications like hand wash and face wash. These are particularly preferred for out-of-home applications such as during travel, at hotels and restaurants where people are more conscious of hygiene, as there is a possibility of contamination at the wash place with formats such as bars when large numbers of people use the same bar one after the other.

Such cleansing compositions have been formulated with detergent actives for providing the cleansing action. Popular detergent actives which have been used are soaps and synthetic surfactants. Soaps are salts of fatty acid of which alkali metal salts have been more commonly used. Of these, potassium soap has been more preferred in such soft solid or liquid cleansing compositions, since potassium soaps are more soluble in water than other soaps, thereby maintaining the liquid state in the formulation.

Synthetic surfactants are usually made from materials of petroleum origin. Synthetic surfactants are classified into anionic, cationic, nonionic, amphoteric and zwitterionic classes. All of the above classes have been included in personal cleansing compositions. Popular synthetic surfactants include primary alcohol sulphates (PAS), alkylbenzene-sulphonates (LAS), sulphates of ethoxylated aliphatic alcohols containing 1-12 ethyleneoxy groups, sodium lauryl ethoxy sulphate (SLES), the reaction product of fatty acids esterified with isethionic acid and neutralised with alkali, alkyl betaines (e.g. cocobetaine), alkyl amidopropylbetaines (e.g. coco amidopropyl betaine—CAPB), sorbiton monostearate, sorbiton monooleate, ethoxylated SLES, cetyl trimethyl ammonium halide among a host of other surfactants, many of which are commercially available under various brand names.

Many of the above mentioned soaps and synthetic surfactants are expensive. It is believed that the surfactants are not effectively utilized, and there is scope for better utilisation, thereby reducing wastage and cost to both the manufacturers and the consumers. Further, conventional surfactants mentioned above are believed to be non-biodegradable, and therefore a burden to the environment. Thus, development of alternative surface active materials which are more environmentally friendly will be welcomed not only by the Governments but by the manufacturers and consumers at large. Conventional surfactants are also perceived by some consumers to harsh on the skin, leave an unpleasant feel on the skin after use and there are problems with ease of rinsing. Thus, there is a need for providing milder, more skin friendly and easily rinse able detergent actives in personal cleansing compositions.

Certain highly absorbent materials like clay e.g. bentonite, attapulgite, kaolinite etc which are known to absorb oils have been used in cleansing compositions, but have had limited usefulness when incorporated in personal cleansing compositions.

There has been further work on functionalising particulate material. Examples of design and synthesis of such particles using the above strategy are described in a review by Perro et al, J. Material Chem., 2005, 15, p 3745-3760. One of the approaches used in the past is disclosed in U.S. Pat. No. 4,715,986 (Th. Goldschmidt AG, 1987) which describes particles for stabilizing or destabilizing emulsions of a size less than 100 microns, comprising fragments having on one side thereof hydrophilic group and on the other side thereof hydrophobic groups such that the hydrophilic and the hydrophobic groups are anisotropically distributed in a non-statistical manner. One of the methods for obtaining such fragments is by communition of hollow microspheres. In all the methods that are described, precursor materials have homogeneous distribution of surface groups, e.g. silica, alumina, hollow microspheres, microgel, carbon and starch. Processes starting with asymmetric particles such as 1:1 clays are not described. The present inventors have been working on solving this problem of providing alternative materials having enhanced surface active properties. They have, during the course of their research, developed novel materials starting from 1:1 or 2:1:1 clays that give materials with enhanced oil removal properties and are therefore highly suitable for preparing liquid or soft solid personal cleaning compositions. Quite surprisingly, these materials could be prepared from inexpensive and widely available materials using simple processes, in high yield with the additional advantage that the processes are easy to scale up. The prior art materials and process known to prepare them were found to suffer from lack of one or more of the above listed advantages.

In view of the limitations in the prior art, one of the objects of the present invention is to overcome or ameliorate at least one of the disadvantages of the prior art, or to provide a useful alternative.

Another object of the present invention is to provide a personal cleansing composition comprising a novel material which is an alternative to conventional surfactant which on the one hand has similar or superior properties compared to conventional surfactants with less of their disadvantages like low biodegradability, irritation to the skin and high cost.

Yet another object of the present invention is to provide for a personal cleansing composition that utilises a novel material which is an alternative to conventional surfactant which can be prepared using simple and easy to scale up process.

According to the present invention, in a first aspect there is provided a liquid or soft-solid personal cleansing composition comprising (i) 1 to 50% of treated clay particles; and (ii) a cosmetically acceptable base;

wherein said treated clay particles are asymmetric 1:1 or 2:1:1 clay particles having alternating tetrahedral and octahedral sheets terminating with a tetrahedral sheet at one external surface plane and an octahedral sheet at another external surface plane, with a fatty acid of carbon chain length 10 to 22 attached to coordinating cation on one of said exterior surface planes.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se.

Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The present invention relates to a liquid or soft solid personal cleansing composition which comprises a novel material having surface active properties. The material is prepared from precursor particles which is are asymmetric 1:1 or 2:1:1 clay particles having alternating tetrahedral and octahedral sheets terminating with a tetrahedral sheet at one external surface plane and an octahedral sheet at another external surface plane. The precursor clay is treated to have bipolar topospecific characteristics, which is achieved by having a fatty acid of carbon chain length 10 to 22 attached to coordinating cation on one of the exterior surface planes i.e. either the external surface plane having the tetrahedral sheet or the external surface having the octahedral sheet. The personal cleaning composition is formulated in a cosmetically acceptable base.

The precursor of the treated particle with bipolar topospecific characteristics according to the present invention is an asymmetric 1:1 or 2:1:1 clay particle having alternating tetrahedral and an octahedral sheets terminating with a tetrahedral and an octahedral sheet at exterior surface planes. Particles of 1:1 clay are particularly preferred as the precursor.

1:1 clays preferred according to the present invention include kaolinite and serpentine subgroups of minerals. The species included within kaolinite subgroup are particularly preferred viz. kaolinite, dickite, halloysite and nacrite.

The species included within serpentine subgroup are chrysolite, lizardite, and amesite.

2:1:1 clays preferred according to the present invention include chlorite group of minerals. Chlorite is also erroneously referred to as a 2:2 clay by some mineralogists. The chlorite comprises tetrahedral-octahedral-tetrahedral sheets like 2:1 clays, with extra weakly bound brucite like layer between tetrahedral layers.

The tetrahedral sheet preferably comprises coordinating tetrahedral cation of silicon. The tetrahedral sheet may also comprise isomorphously substituted coordinating tetrahedral cations which are not silicon. Isomorphously substituted coordinating tetrahedral cations include, but are not limited to, cations of aluminium, iron or boron.

The octahedral sheet preferably comprises coordinating octahedral cation of aluminium. The octahedral sheet may also comprise isomorphously substituted coordinating octahedral cations which are not aluminium. Isomorphously substituted coordinating octahedral cations include cations of magnesium or iron.

It is preferred that the fatty acid is attached to the coordinating cations on the exterior side of one of the external surface sheets. Accordingly, the fatty acid may be attached to coordinating cations on the exterior side of the tetrahedral sheet. Alternatively, the fatty acid is attached to coordinating cations on the exterior side of the octahedral sheet which is the more preferred aspect.

The treated particle used in the personal cleansing composition of the invention is believed to have the property of anisotropic hydrophobicity which is possibly the reason for providing the surface active property responsible for the cleansing action. By anisotropicity is meant that the particle has two spatially distinct exterior faces having distinct surface characteristics wherein one of the distinct exterior faces is relatively more hydrophilic and the other distinct exterior face is relatively more hydrophobic. This is achieved due to the unique property of the chosen precursor clays which provide for selective attachment of the fatty acid on only one of the exterior surface planes.

In addition to providing the cleansing action, the treated particle with bipolar topospecific characteristics of the present invention enables formulation of the treated particles in relatively more stable emulsions as compared to untreated particles at same particle loading. Thus the treated particles also act as useful emulsifying agent in the composition of the invention.

The personal cleaning composition of the invention is easy to rinse off after use, thus having the advantage that a lesser amount of water is required in rinsing the composition after its use.

The treated particles are preferably present in 5 to 30% more preferably 10 to 20% by weight of the composition.

Although fatty acid of carbon chain length 10 to 22 are attached to coordinating cation on one of said exterior surface planes of the particle, it is preferred that the carbon chain length is from 12 to 20. Most preferably the fatty acid is selected from oleic acid, palmitic acid, stearic acid or myristic acid.

The composition of the invention preferably comprises a cosmetically acceptable vehicle. The cosmetically acceptable vehicle is suitably chosen to provide the composition in any one of the well known wash off formats. Well known formats in which the composition of the present invention may be formulated include cream, gel, or lotion. One preferred format is the oil-in-water emulsion which may be cream or lotion, more preferred being cream. Lotions and creams are prepared in very many different consistencies. One measure of consistency is viscosity. Viscosity of a material depends on the shear rate at which it is measured. Lotions usually have a viscosity of 1 to 100 cP at zero shear at 25° C. Creams and gels generally have a viscosity of 100 to 10,000 cP at zero shear at 25° C. Creams have very high yield stress i.e. deform and start to flow only at high applied shear rates. Gels on the other hand have low yield stress i.e. deform and start to flow at low applied shear rates. The invention is directed to preparing a composition in the liquid or soft solid form, hereinabove defined, and is preferably not suitable for preparing a shaped solid cleansing composition.

The cream format preferably comprises 5 to 25% fatty acids. Additionally the cream may comprise 0.1-10%, more preferably 0.1 to 5% fatty acid soap. The most preferred fatty acid for forming the oil-in-water emulsion is stearic acid. The other preferred cosmetically acceptable vehicle is a detergent composition. The detergent composition preferably comprises 5 to 85% salt of fatty acid or 2 to 20% synthetic surfactant or mixture thereof. When the composition is formulated as a cream, the composition preferably comprises 50 to 80% water Another suitable format of the personal cleansing composition of the invention is a gel i.e. the cosmetically acceptable base is a gel. The gel is generally a viscous liquid. The viscosity is achieved through use of a thickening polymer. Thickening polymer is preferably present in 1 to 20% by weight of the personal cleansing composition of the invention. Examples of thickening polymer which may be used are hydroxyl ethyl cellulose, hydroxy propyl methyl cellulose, hydrophobically modified ethoxylated urethane, propylene glycol derivatives or polyacrylic acid more preferably a cross-linked polyacrylic acid. Gel composition generally comprise 50 to 90% water. Similarly, personal cleansing compositions in the lotion format generally comprise 50 to 90% water.

The personal cleansing composition of the invention generally does not require a conventional surfactant for aiding the cleaning action and thus in an optimum proposition the composition is devoid of any conventional surfactant. However the composition may comprise 0.1 to 5% synthetic surfactant.

The treated clay particles for use in a composition of the invention may be prepared by a simple and easy to scale up process. Such a process comprises the steps of (a) contacting asymmetric 1:1 or 2:1:1 clay particles having alternating tetrahedral and octahedral sheets terminating with a tetrahedral sheet at one external surface plane and an octahedral sheet at another external surface plane, with an alkali to increase the pH above 7; (b) adding an alkali metal salt of said fatty acid of carbon chain length 10 to 22, at a temperature between 50 and 150° C.; (c) adding a mineral acid to reduce pH below 7, and (d) separating the treated particles from the reaction mixture.

Clay particles used in the above process for preparing the treated clay particles are preferably chosen from kaolinite, dickite, halloysite and nacrite.

It is particularly preferred that the precursor is first contacted with a mineral acid before contacting with the alkali. The mineral acids which are contacted with the precursor are preferably selected from sulphuric acid, nitric acid or hydrochloric acid, hydrochloric acid being preferred. Preferred concentration of minerals acids are in the range of 0.1 to 0.5 N. It is preferred that the alkali used to increase the pH above 7 is selected from alkali metal hydroxide, carbonate or bicarbonate where the preferred alkali metal is sodium or potassium. Preferred concentration of alkali is from 0.01 to 0.5 N. The fatty acid salt is preferably added at a temperature between 60 to 95° C. The final pH below 7 is preferably between 6 to 6.9. The treated clay particles are separated from the reaction mixture, preferably by filtration.

The liquid or soft solid personal cleansing composition of the invention may comprise an optional ingredient like a skin lightening agent. The skin lightening agent is preferably chosen from one or more of a vitamin B3 compound or its derivative e.g. niacin, nicotinic acid, niacinamide or other well known skin lightening agents. Skin lightening agent, when used, is preferably present in an amount in the range of 0.1 to 10%, more preferably 0.2 to 5% by weight of the personal cleansing composition.

Other optional ingredients in the personal cleansing composition include UV sunscreens e.g. 2-ethylhexyl-p-methoxycinnamate, butyl methoxy dibenzoylmethane, and mixtures thereof. The composition preferably comprises from about 0.1% to about 10%, more preferably from about 0.1% to about 5%, sunscreen agent by weight of the composition. Inorganic UV sunscreens, also called sunblocks, may also be included e.g. zinc oxide, iron oxide, silica, and titanium dioxide. Most suitable sunblocks are zinc oxide or titanium dioxide. The sun block is preferably incorporated in 0.1 to 5% by weight of the composition.

The composition according to the invention may also comprise other diluents. The diluents act as a dispersant or carrier for other materials present in the composition, so as to facilitate their distribution when the composition is applied to the skin.

Diluents other than water can include liquid or solid emollients, solvents, humectants, thickeners and powders.

The cosmetically acceptable vehicle is preferably present from 10 to 99.9%, preferably from 50 to 99% by weight of the composition, and can, in the absence of other cosmetic adjuncts, form the balance of the composition.

The compositions of the present invention can comprise a wide range of other optional ingredients. Examples of such optional ingredients include antioxidants, anti-aging agents, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

The invention will now be demonstrated with the help of the following non-limited examples

EXAMPLES

Examples 1 to 5

Efficacy of the Oil Absorption of the Novel Particles of the Invention as Compared to Known Particles Experiments were conducted as per the following protocol:

About 0.75 gram of desired particles (as per Table 1) were taken in a small beaker. About 0.85 gram of water was added to it and mixed with a spatula to make a paste.

The experiment consisted of taking polyester coated glass slide, which is considered to be a surrogate for skin as the substrate. Olive oil was taken as the substitute for sebum. About 10 µl of olive oil was spread on the polyester coated glass slide. About 20 mg of the paste of the powder prepared earlier was put in the middle of the oil layer on the substrate. The paste was allowed to stay for about 10 seconds and then washed with about 25 ml of water. The substrate was then allowed to dry. The amount of oil remaining on the substrate was measured using a Courage & Khazaka sebumeter. The data on the % oil removed for the various particles are summarised in Table 1. Experiments were done in triplicate and the standard deviation in the data is indicated in Table 1.

Example 1

The particle used was Multani mutti which is Bentonite sourced from Sree Venkateshwara Enterprises. Bentonite is mostly composed of montmorillonite which is a 2:1 type of clay.

Example 2

The particle used was alumina sourced from Acne Synthetic Chemicals, India.

Example 3

Alumina was sourced from Acne Synthetic Chemicals, India. The particles of Alumina were then treated as per the following procedure:

Alumina particles were treated with a solution of sodium hydroxide at a pH of 8.0. At this pH, the particles of alumina were treated with sodium oleate at 90° C. with the weight ratio of alumina to sodium oleate of 1:9 under constant stirring for six hours. The reaction medium was then treated with hydrochloric acid to bring the pH of the reaction medium to 6.3. The particles were then filtered from the reaction media and washed with water and acetate and dried to prepare reacted alumina.

Example 4

The particle used was kaolinite sourced from English India China Clay Co., India. Kaolinite is a 1:1 clay.

Example 5

Kaolinite sourced from English India China Clay Co. India was treated as per the invention using the following procedure:

The kaolinite particles were treated with a solution of sodium hydroxide to a pH of 8.0. At this pH, the particles of kaolinite were treated with sodium oleate at 90° C. with the weight ratio of kaolinite to sodium oleate of 1:9 under constant stirring for six hours. The reaction medium was then treated with hydrochloric acid to bring the pH of the reaction medium to 6.3. The particles were then filtered from the reaction media and washed with water and acetate and dried to prepare the particles as per the invention.

TABLE 1

| Example | Particle | % oil removed, mean | Standard deviation |
|---|---|---|---|
| 1 | Multani mutti | 59 | 14 |
| 2 | Reacted alumina | 57 | 18 |
| 3 | Hydrophobic alumina | 51 | 13 |
| 4 | Kaolinite | 61 | 4 |
| 5 | Particle as per invention | 98 | 5 |

The data in Table 1 indicates that the particle as per the invention provides for significantly higher oil removal efficacy as compared to its precursor and similar particles used in the past.

Examples 6 to 11

Efficacy of Various Gel Compositions as per the Invention as Compared to Similar Compositions where Conventional Surfactants are Used Various formulations as shown in Table 2 were prepared.

TABLE 2

| | Example | | | | | |
|---|---|---|---|---|---|---|
| | 6 | 7 | 8 | 9 | 10 | 11 |
| Polymer | 5.00 | 5.00 | 5.00 | 5.00 | 5.00 | 5.00 |
| NaOH | 1.18 | 1.18 | 1.18 | 1.18 | 1.18 | 1.18 |
| Glycerine | 2.00 | 2.00 | 2.00 | 2.00 | 2.00 | 2.00 |
| Silicone oil | 0.20 | 0.20 | 0.20 | 0.20 | 0.20 | 0.20 |
| Preservative | 0.20 | 0.20 | 0.20 | 0.20 | 0.20 | 0.20 |
| Perfume | 0.10 | 0.10 | 0.10 | 0.10 | 0.10 | 0.10 |
| Active | SLES | Particle | SLES | Particle | SLES | Particle |
| Active, wt % | 5.00 | 5.00 | 10.00 | 10.00 | 15.00 | 15.00 |
| Water | To 100 | To 100 | To 100 | To 100 | To 100 | To 100 |

In the above table:

Polymer: used was a mix of cross linked polyacrylate polymers: Aculyn 88 and Aculyn 44 in a weight ratio of 4:1.

Preservative: used was methyl paraben

SLES: was sodium lauryl ethoxy sulphate having 2 EO groups.

Particle: was the particle prepared as per Example 5.

The compositions were tested for oil removal.

The oil removal efficacy of each of the compositions of Table 2 along with the cost of the compositions is summarised in Table 3.

TABLE 3

| | Example | | | | | |
|---|---|---|---|---|---|---|
| | 6 | 7 | 8 | 9 | 10 | 11 |
| Oil removal, % mean | 100 | 98 | 100 | 96 | 100 | 99 |
| Standard Deviation | 0 | 0 | 0 | 2 | 0 | 1 |
| Cost | 19.6 | 13.0 | 27.1 | 14.0 | 34.6 | 14.9 |

The data in Table 3 indicates that the compositions as per the invention (7, 9 and 11) provide similar cleaning as compared to compositions having same amount of conventional surfactant. This is achieved at much lower cost as compared to use of conventional surfactants The invention thus provides for a liquid or soft solid personal cleansing composition which utilises a material which is an alternative to conventional surfactant which has similar or superior cleaning properties. The new material has less of the disadvantages of conventional surfactants which are low biodegradability, irritation to the skin and high cost.

Further, the material can be prepared using a simple and easy to scale up process.

The invention claimed is:

1. A liquid or soft-solid personal cleansing composition comprising
    (i) 1 to 50% of treated clay particles; and
    (ii) a cosmetically acceptable base;
wherein said treated clay particles are asymmetric 1:1 or 2:1:1 clay particles having alternating tetrahedral and octahedral sheets terminating with a tetrahedral sheet at one external surface plane and an octahedral sheet at another external surface plane, with a fatty acid of carbon chain length 10 to 22 attached to coordinating cation on one of said exterior surface planes.

2. A composition as claimed in claim 1 wherein said fatty acid is attached to an external surface plane having an octahedral sheet.

3. A composition as claimed in claim 1 wherein said fatty acid is selected from oleic, palmitic, stearic or myristic acid.

4. A composition as claimed in claim 1 wherein said cosmetically acceptable base is an oil-in-water emulsion.

5. A composition as claimed in claim 4 wherein the emulsion comprises 5 to 25% fatty acid.

6. A composition as claimed in claim 5 wherein said emulsion comprises 0.1 to 10% fatty acid soap.

7. A composition as claimed in claim 1 wherein said composition comprises 50 to 80% water.

8. A composition as claimed in claim 1 wherein said cosmetically acceptable base is a gel.

9. A composition as claimed in claim 8 wherein said gel comprises 1 to 20% of a thickening polymer.

10. A composition as claimed in claim 9 wherein said thickening polymer is a crosslinked polyacrylic acid.

11. A composition as claimed in claim 1 comprising 50 to 90% water.

12. A composition as claimed in claim 1 comprising 0.1 to 5% synthetic surfactant.

13. A composition as claimed in claim 1 wherein said fatty acid is oleic acid.

14. A composition as claimed in claim 1 wherein the treated clay is prepared by a process that comprises the steps of:
    (a) contacting asymmetric 1:1 or 2:1:1 clay particles having alternating tetrahedral and octahedral sheets terminating with a tetrahedral sheet at one external surface plane and an octahedral sheet at another external surface plane, with an alkali to increase the pH above 7;

(b) adding an alkali metal salt of said fatty acid of carbon chain length 10 to 22, at a temperature between 50 and 150° C.;

(c) adding a mineral acid to reduce pH below 7, and (d) separating the treated particles from the reaction mixture.

* * * * *